United States Patent
Klein et al.

(10) Patent No.: US 9,192,454 B2
(45) Date of Patent: Nov. 24, 2015

(54) ORTHOSIS COMPRISING AN UPPER TRAY AND A LOWER TRAY, AND CONNECTION WITH ADJUSTABLE POSITIONING

(75) Inventors: Dominico Klein, Rennes (FR); Dominique Perlade, Vigneux de Bretagne (FR)

(73) Assignee: MEDVENTIV, Rennes (FR)

( * ) Notice: Subject to any disclaimer, the term of this patent is extended or adjusted under 35 U.S.C. 154(b) by 0 days.

(21) Appl. No.: 13/810,390

(22) PCT Filed: Jul. 18, 2011

(86) PCT No.: PCT/EP2011/062284
§ 371 (c)(1),
(2), (4) Date: Nov. 8, 2013

(87) PCT Pub. No.: WO2012/010565
PCT Pub. Date: Jan. 26, 2012

(65) Prior Publication Data
US 2014/0120489 A1  May 1, 2014

(30) Foreign Application Priority Data

Jul. 20, 2010  (FR) .................................... 10 03041

(51) Int. Cl.
*A61C 3/00* (2006.01)
*A61C 7/36* (2006.01)
*A61F 5/56* (2006.01)
*A61C 7/08* (2006.01)

(52) U.S. Cl.
CPC ... *A61C 7/36* (2013.01); *A61C 7/08* (2013.01); *A61F 5/566* (2013.01)

(58) Field of Classification Search
CPC .................................... A61C 7/08; A61C 7/36
USPC ..................................... 433/6; 128/859, 861
See application file for complete search history.

(56) References Cited

U.S. PATENT DOCUMENTS 5,365,945 A * 11/1994 Halstrom ....................... 128/848
5,722,828 A *  3/1998 Halstrom ......................... 433/69
(Continued)

FOREIGN PATENT DOCUMENTS

DE  10042049 A1 *  3/2002  ............... A61C 7/36
EP     0801937 A1    10/1997
(Continued)

OTHER PUBLICATIONS

International Search Report dated Oct. 20, 2011 for corresponding International Application No. PCT/EP2011/062284, filed Jul. 18, 2011.
International Preliminary Report on Patentability and English translation of Written Opinion dated Jan. 22, 2013 for corresponding International Application No. PCT/EP2011/062284, filed Jul. 18, 2011.

*Primary Examiner* — Cris L Rodriguez
*Assistant Examiner* — Mirayda A Aponte
(74) *Attorney, Agent, or Firm* — David D. Brush; Westman, Champlin & Koehler, P.A.

(57) ABSTRACT

An orthosis includes an upper tray and a lower tray, which are designed to line the teeth of an upper jaw and the teeth of a lower jaw, respectively. A connection joins the trays. The upper tray has at least a first fixed base, and the lower tray has at least a second fixed base. The connection has a fixed length and is designed to be fixed, on the one hand, to the first base and, on the other hand, to the second base, in a position that has an advancing effect and that is adjustable by way of a control element integrated in at least one of the two bases.

9 Claims, 2 Drawing Sheets

(56) References Cited

U.S. PATENT DOCUMENTS

| | | | |
|---|---|---|---|
| 6,041,784 A * | 3/2000 | Halstrom | 128/848 |
| 6,161,542 A * | 12/2000 | Halstrom | 128/848 |
| 6,767,207 B1 * | 7/2004 | Lampert | 433/6 |
| 2005/0016547 A1 * | 1/2005 | Mousselon et al. | 128/861 |
| 2006/0174897 A1 * | 8/2006 | Sarkisian | 128/859 |
| 2008/0072915 A1 * | 3/2008 | Nelissen | 128/848 |
| 2009/0090371 A1 * | 4/2009 | Toussaint | 128/848 |
| 2010/0065067 A1 * | 3/2010 | Lee | 128/848 |
| 2010/0261133 A1 * | 10/2010 | Lax | 433/71 |
| 2012/0214120 A1 * | 8/2012 | Marcus | 433/19 |

FOREIGN PATENT DOCUMENTS

| | | | |
|---|---|---|---|
| EP | 1867309 A1 * | 12/2007 | A61F 5/56 |
| FR | 2820307 A1 | 8/2002 | |
| WO | 02062252 A1 | 8/2002 | |
| WO | 03034957 A2 | 5/2003 | |

* cited by examiner

US 9,192,454 B2

ORTHOSIS COMPRISING AN UPPER TRAY AND A LOWER TRAY, AND CONNECTION WITH ADJUSTABLE POSITIONING

CROSS-REFERENCE TO RELATED APPLICATIONS

This Application is a Section 371 National Stage Application of International Application No. PCT/EP2011/062284, filed Jul. 18, 2011, which is incorporated by reference in its entirety and published as WO 2012/010565 on Jan. 26, 2012, not in English.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The disclosure relates to the field of the design and production of orthopedic and/or orthodontic devices. More specifically, the disclosure relates to a removable-type prefabricated orthosis.

The specialty of DFO (dentofacial orthopedics), commonly called orthodontics, is aimed at the prevention and the correction of dental malalignments and the establishment of optimal inter-dental contact. It applies both to restoration of the appearance of the face by means of the maxillae (commonly called "jaws") and to correction of functions such as respiration, chewing and speech.

Orthodontics treats malalignments of the teeth, and is intended to position them in an aesthetically and functionally harmonious manner on the dental arches.

After correction of the malalignments using fixed apparatuses, in particular in the form of attachments glued to the crown of the teeth, the dentition is subjected to a muscular environment (the dental arches are located at the center of an internal muscular wall: the tongue and another lateral external muscular wall: the cheeks formed by the buccinator muscles and an antero-external muscular wall: the muscles of the lips and in particular the orbicularis), which changes and, therefore, does not ensure the stability and the result of the correction.

A phase of maintaining the result is thus essential: this is retention.

Retention is ensured either by fixed devices glued to the teeth or by removable devices.

Among the removable devices, there are trays placed independently on each dental arch, or double trays, prefabricated and treating both dental arches simultaneously in a "positioner" role.

The disclosure relates to removable-type orthoses, with a double tray, for post-orthodontic treatment retention.

It is noted that an orthosis according to the disclosure may also be used, in simple and benign cases, for the treatment of obstructive sleep apnea syndrome (OSAS), or for the treatment intended to prevent problems of functional origin: it is then an interception and guiding apparatus.

BACKGROUND OF THE DISCLOSURE

In the field of the disclosure, a plurality of types of double-tray orthoses have been proposed in the prior art.

In particular, an orthosis as described by the patent document FR 2 820 307 is known, formed by two trays in a general U shape, namely a lower so-called mandibular tray and an upper so-called maxilla tray, each of which has individual tooth cells and comprising projecting elements with complementary shapes, capable of engaging with one another to ensure the connection of the trays. The projecting elements are of the mortise and tenon type, preferably with a dovetail.

It is thus possible to attach the lower tray with the upper tray with a possible adjustment in the anteroposterior direction.

This solution has, in particular, the following disadvantages:

- the projecting elements with engagement by resilient deformation do not enable a reliable connection, and the user may thus separate the lower tray from the upper tray, then put them back together in a possibly inappropriate position;
- the projecting elements by simple assembly or by bonded assembly do not ensure that the upper and lower trays will remain permanently secured when the device is placed in the mouth, thereby making the retainer inoperative;
- in a possible mass production by plastic injection, the mortise and tenon system may be expensive to industrialize.

Another orthosis described by the patent document published under number WO 03/034957 is known, which describes an intra-oral orthosis including:

- an upper tray and a lower tray intended to respectively cover the teeth of an upper jaw and the teeth of a lower jaw;
- two ties retaining the trays, which ties have a length so that the lower jaw is held in an advanced position with respect to the upper jaw.

In this solution, the ties have means enabling their length to be adjusted. A number of solutions are proposed for producing ties with a variable length, namely:

- the ties have two threaded passages in which a rod is screwed, the ends of which have a reverse pitch, with a nut being placed at the center of the rod;
- the ties include a cylinder in which a rod having an end including a piston slides under the action of a hydraulic pressure;
- the ties include two bars sliding one into the other, each being equipped with a drilling.

Such solutions have, in particular, the following disadvantages:

- the ties are small mechanical parts, requiring relatively precise machining, which tends to make the production of ties expensive;
- the ties may have projecting portions capable of causing small cuts in the person wearing the orthosis.

SUMMARY

An exemplary embodiment of the present invention relates to relates to an orthosis including:

- an upper tray and a lower tray intended to respectively cover the teeth of an upper jaw and the teeth of a lower jaw;
- a connection linking the trays, characterized in that said upper tray has at least one first fixed base, in that said lower tray has at least one second fixed base, and in that said connection includes said first and second bases, which have complementary shapes so that one of the bases forms a sliding guide of the other, according to an adjustable positioning with advancing effect.

Thus, owing to an exemplary embodiment of the invention, the orthosis is appropriately adjusted to the patient's needs, without it being possible for the patient to inadvertently modify this adjustment, as will be shown more clearly below.

Moreover, the connection of an orthosis according to an embodiment of the invention can be produced simply, inexpensively, insofar as they have a fixed length and do not therefore include portions capable of moving with respect to one another.

The connection is also inexpensive to produce insofar as the means for adjusting the position between the two trays is integrated with at least one of the bases integrated with the trays, and not directly on additional connection elements such as those mentioned in reference to the prior art.

According to a first embodiment, said first base has a slide track, with said second base forming a slide capable of sliding in said slide track.

According to a second embodiment, said second base has a slide track, with said first base forming a slide capable of sliding in said slide track.

In one or the other case, said first base and said second base are intended to be secured by at least one screw, said screw preferably being self-tapping. In addition, such a screw is preferably "self-locking" owing to an optimal screw pitch.

According to a first alternative embodiment, said first base has a single screw passage while said second base has at least two screw passages intended to be one or the other placed so as to coincide with the single passage of the first base.

According to a second alternative embodiment, said second base has a single screw passage while said first base has at least two screw passages intended to be one or the other placed so as to coincide with the single passage of the second base.

According to an advantageous solution, each base includes a base forming a coupling element with one of the trays, with said slide track or said slide extending from said base.

According to a particular embodiment, one of said bases has one and/or the other of the following features:
- it has a series of screw passages enabling an adjustment of the positioning with advancing effect over a 10 mm stroke;
- it has a series of screw passages enabling an adjustment of the positioning with advancing effect with a 2 mm pitch.

According to another feature of an embodiment of the invention, said upper tray has a first contact surface and said lower tray has a second contact surface bearing against said first contact surface according to a contact plane with a slope corresponding to the direction of adjustment of the positioning with advancing effect of the connection.

BRIEF DESCRIPTION OF THE DRAWINGS

Other features and advantages will become clearer in view of the following description of an embodiment of the invention, provided as an illustrative and non-limiting example, and the appended drawings, wherein.

DETAILED DESCRIPTION OF ILLUSTRATIVE EMBODIMENTS

Figure 1:
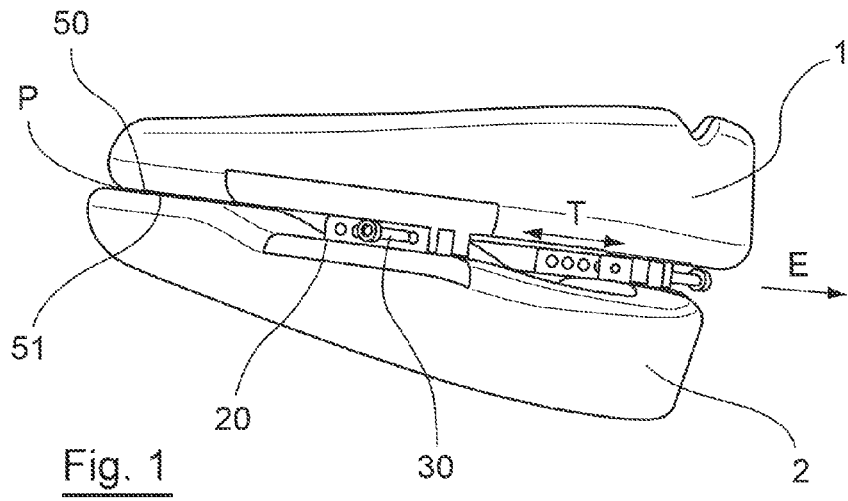
FIG. 1 is a perspective view of an orthosis according to an embodiment of the invention.

As indicated above, the principle of an embodiment of the invention lies in the fact of proposing an orthosis wherein the connection connecting the upper tray to the lower tray are adjustable in position so as to provide a variable (adjustable) advancing effect, by way of integrated adjustment means on at least one of the two trays.

In reference to FIGS. 1 to 4, an orthosis according to an embodiment of the invention includes:
- an upper tray 1 intended to cover the teeth of an upper jaw;
- a lower tray 2 intended to cover the teeth of a lower jaw;
- inter-arch connection linking the trays, described in greater detail below.

According to the principle of an embodiment of the invention, the orthosis is designed as follows:
- the upper tray 1 has a first fixed base;
- the lower tray 2 has a second fixed base 20;

The adjustment of the positioning of the connection in order to cause the advancing effect to vary is enabled by way of adjustment means integrated with at least one of the two bases.

The inter-arch connection is formed by the association of the upper and lower bases, and are intended for normal occlusion or advancement.

The adjustment of the positioning of the connection in order to cause the advancement force to vary is enabled by way of sliding means resulting from the complementary shapes of the upper bases and the lower bases.

As shown in FIGS. 2 to 5, the upper base 10 includes:
- a base 100 forming an element for coupling by means of which the upper base is secured to the upper tray;
- a slide track 102 formed by two bosses 101 spaced apart from one another and of which the walls facing one another define the slide track 102.

The bosses 101 each have a through-hole 103, the through-holes 103 of the two bosses of the same base being coaxial.

The second base includes:
- a base 200 forming a coupling element, by means of which the base is secured to the upper tray 2;
- an elongate slide 201, having, over its length, a plurality of through-holes 202.

The slide track 102 and the slide 201 have complementary shapes so that the upper base forms means for guiding a slide 201 in translation between the bosses 101 of the first base.

It is noted that, according to the alternatives capable of being envisaged, the upper/lower position of the different members may vary, for example:
- the slide may be provided on the base of the upper tray, the slide track then being provided on the base of the lower tray;
- the bosses forming the slide track may be elongate and have a plurality of holes (the slide then being capable of having a reduced length, optionally with a single through-hole).

As an indication, the trays 1, 2 are made either of elastomer or thermoplastic; the materials used are medical-grade biocompatible materials. These materials may have different hardnesses.

The bases 10, 20 are made of medical-grade biocompatible thermoplastic materials, and are directly integrated with the trays to form with them a single-piece assembly.

The connection is also designed so as to have a low bulk, and in particular a low tongue overlap.

As indicated above, the inter-arch connection is formed by the association of the first and second bases, preferably by an anti-loosening assembly by means of micro-screws with an optimal screw pitch, capable of being unscrewed by a special screwdriver. The screws 3 used are made of a medical-grade biocompatible metal material.

To adjust the positioning of the upper tray with respect to the lower tray, the slide of one of the bases is engaged in the slide track of the other base. The slide is caused to slide in the slide track so as to obtain the desired adjustment, by placing one of the holes 202 of the second base (or the first base, depending on the case) with the hole (or one of the holes, depending on the case) of the first base (or the second base, depending on the case).

It is of course understood that each through-hole, whether it is that with the bosses forming the slide track or that or those of the slide, forms a passage for an attachment screw 3.

Preferably, the bosses 101 forming the slide track 102 are spaced apart from one another so as to form a recess capable of fitting the slide of the other base. More specifically, the sliding connection between the two bases is obtained by causing the first and second bases (slide track and slide) to coincide concomitantly so that the slide becomes locked in the slide track.

The positioning is then fixed by the attachment screws, which are first inserted into the external boss of the first base, the screw passing through the chosen through-hole of the slide, then being screwed by self-tapping into the internal boss of the slide track.

The diameter of the through-hole of the internal boss is therefore adapted to the diameter of the attachment screw, by being smaller than it so that the screw performs a self-tapping of the internal boss.

Figure 2:
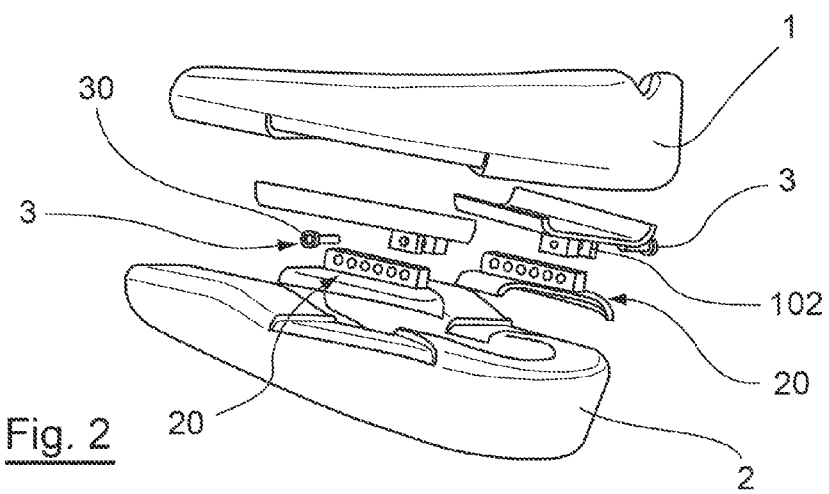
FIG. 2 is an exploded perspective view of an orthosis according to an embodiment of the invention.
Figure 3:
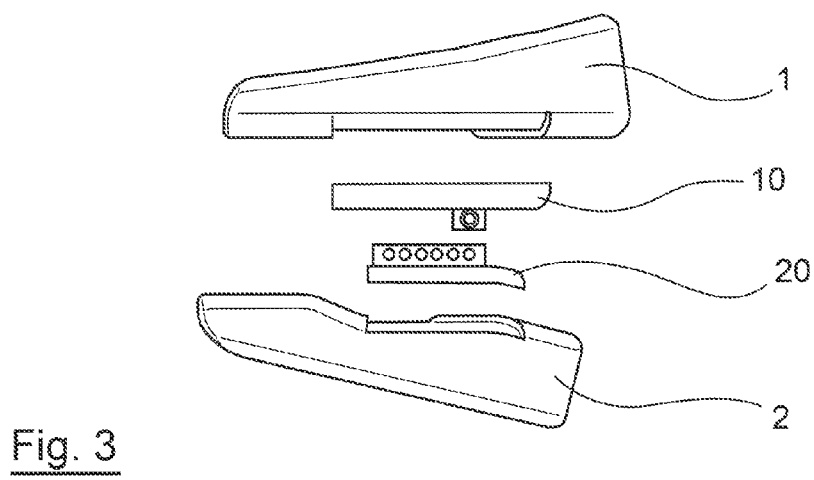
FIG. 3 is an exploded side view of an orthosis according to an embodiment of the invention.
Figure 4:
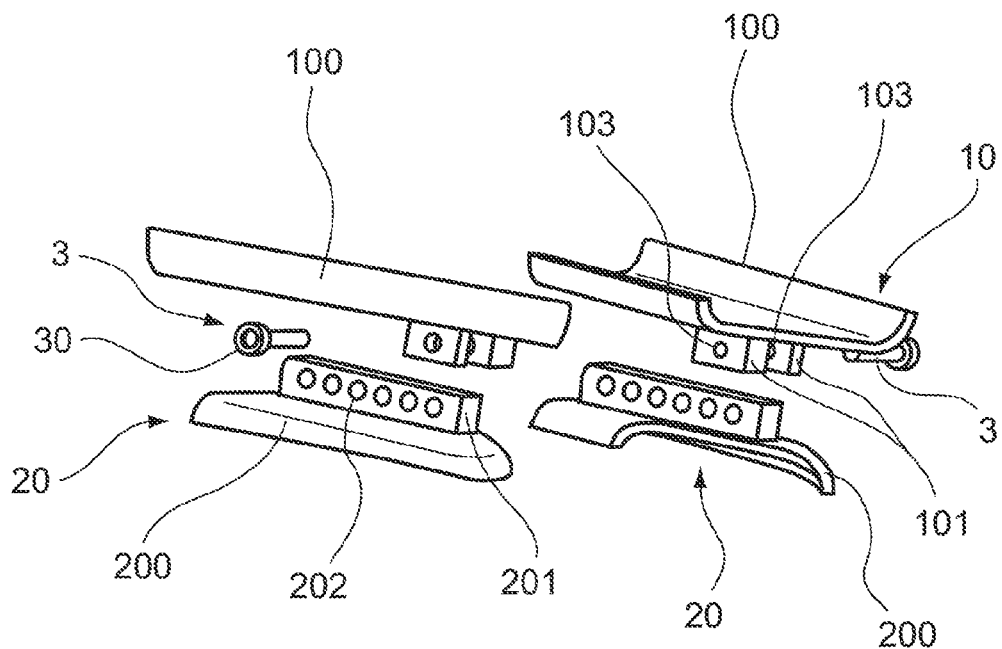
FIG. 4 is a perspective view of inter-arch means of an orthosis according to an embodiment of the invention.
Figure 5:
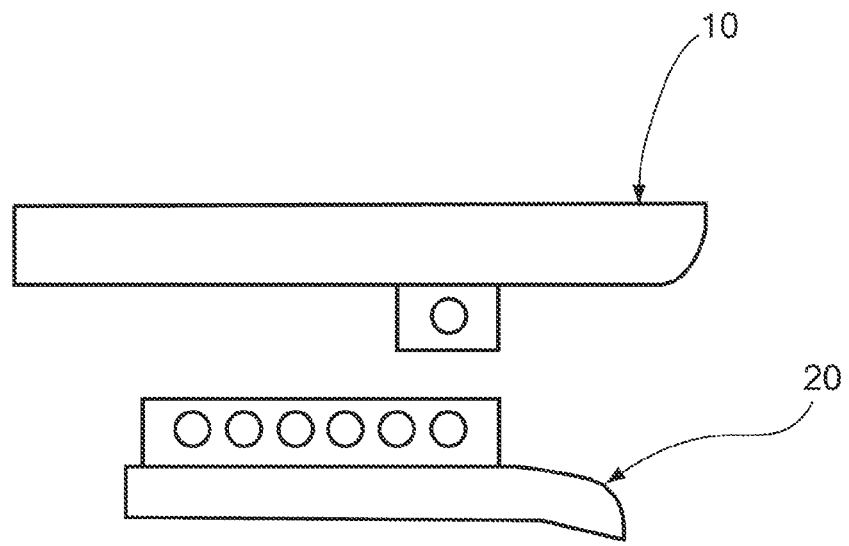
FIG. 5 is a side view of the inter-arch means of an orthosis according to an embodiment of the invention.

The attachment screws are therefore introduced from the outside to the inside of the orthosis as indicated by the position of the head 30 of the screws 3 in FIGS. 1 to 3.

According to a preferred arrangement, the orifices 202 are arranged as follows:
 they enable an adjustment of the positioning with advancement of the connection over a 10 mm stroke;
 they have, between them, a distance of 2 mm, thus predetermining the adjustment pitch.

In addition, the upper tray has a first contact surface 50 and the lower tray 2 has a second contact surface 51, bearing against the first contact surface 50 according to a contact plane P of which the slope corresponds to the direction of adjustment T of the positioning with advancement E of the connection.

In reference to FIG. 1, the first contact surface 50 of the upper tray corresponds to the lower edge of the upper tray. The second contact surface 51 of the lower tray is provided in the rear portion, in the form of a protuberance.

The translation of the lower tray with respect to the upper tray is thus facilitated by the contact areas (surfaces 50, 51), which are parallel to the axis of translation (indicated by the double arrow T).

An exemplary embodiment of the present disclosure therefore relates to an orthosis in which the connection between the lower tray and the upper tray may be produced in an inexpensive manner.

An embodiment also provides such an orthosis that provides a satisfactory level of comfort and quality of treatment for the patient.

Although the present disclosure has been described with reference to one or more examples, workers skilled in the art will recognize that changes may be made in form and detail without departing from the scope of the disclosure and/or the appended claims.

The invention claimed is:

1. An orthosis including:
 an upper tray and a lower tray configured to respectively cover teeth of an upper jaw and teeth of a lower jaw, wherein the upper tray has at least one first fixed base and the lower tray has at least one second fixed base; and
 a connection of said first base to said second base, wherein said first and second bases have complementary shapes so that one of the bases forms a sliding guide of the other, according to an adjustable positioning with an advancing effect, said connection being securable so as to prevent any movement between the upper tray and the lower tray when the orthosis is in place in the mouth of a patient,
 wherein said first base and said second base are secured to each other by at least one screw; and
 wherein:
  said first base has a single screw passage while said second base has at least two screw passages configured to be one or the other placed so as to coincide with the single screw passage of the first base, or
  said second base has a single screw passage while said first base has at least two screw passages configured to be one or the other placed so as to coincide with the single screw passage of the second base.

2. The orthosis according to claim 1, wherein said first base has a slide track and said second base forms a slide capable of sliding in said slide track.

3. The orthosis according to claim 2 wherein each of said first base and said second base forms a coupling element with one of the trays, with said slide track or said slide extending from said coupling element.

4. The orthosis according to claim 1, wherein said second base has a slide track and said first base forms a slide capable of sliding in said slide track.

5. The orthosis according to claim 4 wherein each of said first base and said second base forms a coupling element with one of the trays, with said slide track or said slide extending from said coupling element.

6. The orthosis according to claim 1, wherein said screw is self-tapping.

7. The orthosis according to claim 1, wherein one of said first and second bases has a series of screw passages enabling an adjustment of positioning with an advancing effect of the connection between the first and second bases over a 10 mm stroke.

8. The orthosis according claim 1, wherein one of said first and second bases has a series of screw passages enabling an adjustment of the positioning with advancing effect with an 2 mm pitch.

9. The orthosis according to claim 1, wherein said upper tray has a first contact surface and said lower tray has a second contact surface bearing against said first contact surface according to a contact plane with a slope corresponding to a direction of adjustment of the positioning with advancing effect of the connection.

* * * * *